United States Patent [19]
Murayama

[11] Patent Number: 6,143,695
[45] Date of Patent: Nov. 7, 2000

[54] PLANT-ROOT GROWTH PROMOTING AGENT

[75] Inventor: Akira Murayama, Morotomi-machi, Japan

[73] Assignee: Ajinomoto Co., Inc., Tokyo, Japan

[21] Appl. No.: 08/962,688

[22] Filed: Nov. 3, 1997

[30] Foreign Application Priority Data

Nov. 11, 1996 [JP] Japan ................................. 8-298550
Mar. 14, 1997 [JP] Japan ................................. 9-061006

[51] Int. Cl.$^7$ .................................................. A01N 43/90
[52] U.S. Cl. ............................................................ 504/241
[58] Field of Search ................................................ 504/241

[56] References Cited

U.S. PATENT DOCUMENTS

| | | | |
|---|---|---|---|
| 4,436,547 | 3/1984 | Sampson | 71/76 |
| 5,211,738 | 5/1993 | Sasaki et al. | 504/241 |

FOREIGN PATENT DOCUMENTS

| | | |
|---|---|---|
| 39 10 061 | 10/1990 | Germany. |
| 47-5 | 1/1972 | Japan. |
| 47-20946 | 6/1972 | Japan. |

OTHER PUBLICATIONS

Lobov et al. CA Abstract 72:110109 of Growth of *Parthenocissus tricuspidata* and Rubus tissue in vitro dependent on purine and pyrimidine bases and on maleic acid hydrazide. Fiziol Biokhim Kul't Rast. 1(3):284–9, 1969.

Koda et al. Biosys Abstract 84:181748 of "Cytokinin production by tomato *Lycopersicon esculendum* root nutritional and hormonal factors affecting the amount of cytokinin released from the roots" J. Fac. Agric. Hokkaido Univ. 61(2):261–271, 1983.

Derwent Abstracts, AN 89–282516, JP 01 207 209, Aug. 21, 1989.

Derwent Abstracts, AN 74–59229V, JP 49 027 798, Jul. 20, 1974.

Chemical Abstracts, vol. 85, No. 7, Aug. 16, 1976, AN 42078, Y. Ito, et al., "Studies on the Physiological Responses of Crop Plants Following Application of Exogenous Nucleic Acid Components".

Chemical Abstracts, vol. 114, No. 25, Jun. 24, 1991, AN 242821, CN 1 045 683, Oct. 3, 1990.

Derwent Abstracts, AN 72–39184T, JP 47 020 946, 1972.

Derwent Abstracts, AN 72–03031T, JP 47 000 005, 1972.

Chemical Abstracts, vol., 144 (1991), Abstract No. 242821h.

Tokyo University of Agriculture, vol. 20, No. 1, pp. 35–42. (Japanese) See attached 2927269, 1972.

*Primary Examiner*—S. Mark Clardy
*Attorney, Agent, or Firm*—Oblon, Spivak, McClelland, Maier & Neustadt, P.C.

[57] ABSTRACT

Herein are disclosed, a plant-root growth promoting agent, which comprises inosine as the effective ingredient, as well as a method for promoting plant root growth, which comprise applying such plant-root growth promoting agent to the soil or, in the case of hydroponics, to the hydroponic water.

13 Claims, No Drawings

PLANT-ROOT GROWTH PROMOTING AGENT

BACKGROUND OF THE INVENTION

1. Field of the Invention

The present invention relates to a growth promoting agent for the root of a plant whose roots, stems and leaves can be distinguished each from the other two. More specifically, this invention relates to a plant-root growth promoting agent comprising inosine as the effective ingredient and also to a method for promoting the root growth of such a plant, which method comprises applying inosine as the effective ingredient thereto, as well as to the plant bodies, including leaves of leaf vegetables and fruit of fruit vegetables, of plants to which such a plant-root growth promoting agent has been applied during their life time.

2. Discussion of the Background

Several examples where a nucleic acid-related substance is applied to plants are conventionally known.

For example, in (a) Japanese Patent Publication kokoku No. 22919/1964 is disclosed a plant growth regulator which comprises, as effective ingredients, β-indoleacetic acid or the like and at least one substance selected from the group consisting of a purine base, pyrimidine base, nucleoside and nucleotide, each available by the decomposition of nucleic acid.

In the above plant growth regulator, however, nucleic acid bases, nucleosides and nucleotides which are obtained by the decomposition of nucleic acid and differ in the decomposition degree are treated as substances having the same effects (i.e., equivalents). As is apparent from the disclosure therein that these decomposition products of nucleic acid except some products belonging to purine base do not have substantial plant growth regulating action, the plant growth regulator is a composition which requires, as the essential condition, the combined use of a nucleic-acid decomposition product and β-indoleacetic acid or the like. In addition, the plant growth regulator is applied by (1) immersing seeds, radicles or seed tubers in a solution of the regulator; (2) spraying the solution to young fruit bodies of mushroom, young fruits, floral organs or phylloplanes; or (3) employing the above two treatments in combination at appropriate times selected as needed (for example, subjecting seeds to the immersing treatment, and then the phylloplanes of the plants grown from the seeds to the spraying treatment), which treatments are utterly different from the application method according to the present invention in which the growth promoting agent is applied in such a way that it promotes directly the growth of plant roots.

In (b) Japanese Patent Publication kokoku No. 16310/1974 is disclosed a growth regulator for fruit vegetables which comprises, as effective ingredients, a plant hormone such as chlorophenoxyacetic acid and at least one substance selected from the group consisting of non-decomposed nucleic acid pyrimidine bases, purine bases, nucleosides and nucleotides, the last four being obtainable by the decomposition of nucleic acid.

In this growth regulator for fruit vegetables, however, non-decomposed nucleic acid per se and various decomposition products thereof different in decomposition degree are put in the same category and besides, as is apparent from the disclosure therein that these nucleic-acid related substances are used in order to reduce the generation of various physiological disorders of crops caused by the application of the above-described plant hormone and to increase the expected effects to be brought by the application of the plant hormone, the combined use of a plant hormone and a nucleic-acid related substance is the essential condition. In addition, a solution of the above growth regulator for fruit vegetables is desired to be distributed onto the plant body; this distribution treatment is effected at the flowering season to such an extent of wetting the flower clusters or flower organs with the solution by spraying the solution with the use of a sprayer over the flower clusters, the flower organs or the whole crop or by coating or immersing the flower clusters or flower organs with or in the solution. These treatments are utterly different from the application method of the plant-root growth promoting agent of the present invention.

In (c) Japanese Patent Publication kokoku No. 17670/1979 is disclosed a method for improving the leaf life of a foliage plant, which comprises bringing the leaves, the leaf stems or petioles, or the cut ends thereof, of a matured foliage plant into contact with one or more than one of nucleotides and nucleosides (inosine being given as an example).

Also in the above method for improving the leaf life of a foliage plant, however, various nucleotides and nucleosides are put in the same category and a solution of effective ingredient(s) is applied as described above, which application is utterly different from the method according to the present invention.

In (d) Japanese Patent Application Laid-Open kokai No. 56759/1973 is disclosed a method for promoting the germination of pollen of a fruit tree, which comprises spraying the flower buds of the fruit tree at its bud time with a single solution or a mixed solution of at least two of nucleotides, nucleosides (inosine being given as an example) and nucleic acid bases.

Also in the above method for promoting the germination of pollen of a fruit tree, however, various nucleotides and nucleosides are put in the same category and in addition, a solution of the effective ingredient(s) is applied as described above, which application is utterly different from the application method of the present invention.

In (e) Japanese Patent Laid-Open kokai No. 68848/1985 is disclosed a method for prolonging the life of cut flowers, which comprising applying a mixed solution of inosine and calcium chloride (as a liquid used for natural flowers displayed at a flower shop or a liquid poured in a flower bowl or vase) onto natural flowers.

In the above method for prolonging the life of cut flowers, however, the combined use of inosine and calcium chloride is the essential condition and moreover, the application method of the effective ingredients is utterly different from that of the present invention.

As has been described above, the use of nucleic-acid related substances for plants is conventionally known, but in the said use, the combined use of these substances with other substance is the essential condition. Even if various nucleic-acid related substances are used singly, they are put in the same category without being distinguished from each other. In addition, the application method of effective ingredients is utterly different from that of the present invention.

SUMMARY OF THE INVENTION

The growth of roots is an important basis for plants to grow further. Based on the sound growth of roots, the plant extends its leaves, puts forth flower buds, is pollinated, bears fruit, and enlarges the fruit. From such a viewpoint, there has accordingly been a demand for the development of a new substance or composition, or a new method of promoting the growth of plant roots.

An object of the present invention is therefore to provide a novel growth promoting agent composition for plant roots and a novel method for promoting the growth of plant roots.

With a view to attaining the above object and other objects, the present inventor has carried out an extensive investigation and for the first time found that inosine has marked effects on the growth of roots of the aforesaid plants at large. Based on such findings, the invention has been completed.

The present invention therefore relates to a plant-root growth promoting agent comprising inosine as the effective ingredient, a method for promoting the growth of plant roots, which comprises applying such a plant-root growth promoting agent to the soil or, in the case of hydroponics, to the hydroponic water, and to the plant bodies, including leaves of leaf vegetables and fruit of fruit vegetables, of plants to which such a plant-root growth promoting agent has been applied during their life time.

By the terms "plant-root growth promoting" is meant in this specification that plant roots are increased in number, length (long or short) and/or thickness (slender or corpulent), compared with cases where the plant-root growth promoting agent of the present invention is not used, the other conditions being the same. The terms also include the stimulation or promotion of plant root germination.

DETAILED DESCRIPTION OF THE INVENTION

The present invention will hereinafter be described more specifically.

Plants to which the plant-root growth promoting agent of the present invention is to be applied can be those plants at large which have clearly differentiated roots, stems and leaves, and specific examples thereof include leaf vegetables, fruit vegetables, root vegetables, flowers, fruit trees and grains.

Inosine does not necessarily need to be a purified product. Insofar as it is free from side effects, an inosine product can be an inosine fermentation broth per se. Also, it can take the form such as a concentrate or concentrated and dried product of an inosine fermentation broth, a crude product of inosine separated from an inosine fermentation broth, an inosine-containing intermediate treatment fraction upon the preparation of a nucleic-acid related substance (nucleotide, nucleoside, nucleic acid base, etc.) by the decomposition of nucleic acid, an inosine-containing fraction of a processed inosine fermentation broth or the like. It is needless to say that in the case where the application of inosine is carried out by adding it to hydroponic water, for the purpose of preventing it from contaminating the hydroponic water, thereby causing putrefaction thereof, is preferred the application of inosine in the form free from impurities which may cause pollution or putrefaction.

It is possible that the plant-root growth promoting agent containing inosine as the effective ingredient can be formed into a liquid preparation in which the agent has been dissolved or dispersed in a suitable solvent such as water so as to carry out its application through soil or hydroponic water conveniently or can be formed into a powder or granular preparation by using a proper extender or binder. From the viewpoints of preventing putrefaction or increasing inosine solubility, it is preferred to form inosine into its alkaline aqueous solution which has been added with an inorganic alkali such as alkali metal hydroxide, e.g., NaOH or KOH, alkaline earth metal hydroxide, e.g., $Mg(OH)_2$, or a basic amino acid such as lysine or arginine. Incidentally, when a K-containing compound such as KOH is used, the K component is also considered to have a good influence on the growth of the roots.

Examples of the application method of such a plant-root growth promoting agent include applying the agent to the soil in advance, then followed by sowing it with plant seeds, and adding the agent to hydroponic water to dissolve the former in the latter in the case of hydroponic cultivation.

In addition, the agent can be useful for the purpose of recovering a fruit vegetable such as strawberry or melon from the exhaustion attributed to fruit bearing, or preventing the fruit bearing exhaustion. And, other examples of the application method include applying the agent at a proper time during cultivation, for example, by adding to the soil at the roots of the fruit vegetable or by adding it to the hydroponic water when the symptoms of bearing exhaustion are observed or when bearing exhaustion is expected even if there are no actual symptoms thereof observed.

Proper application amounts vary with the time of application, the kind or cultivation density of the plant, growth or cultivation stage, or the like. Anyway, it is to be noted in this connection that the plant-root growth promoting agent according to the present invention is used in an amount which permits rooting (i.e., root germination) or root growth superior to those of a plant cultivated under the same conditions except that the plant-root growth promoting agent of the present invention has not been applied. This amount can be determined by some preliminary comparison test which is feasible by those skilled in the art. In the case of soil before sowing, for example, the concentration of the inosine moiety can be as low as 5 to 50 g per 100 tons of soil (0.05 to 0.5 ppm). In the case of hydroponic cultivation, the concentration of inosine can be set at 0.1 to 2 ppm per hydroponic water, different from the case of the application to soil. The agent of the present invention therefore exhibits plant rooting action or plant-root growth promoting action at such low concentrations.

Gibberellin which is one of representative plant hormones causes disorders in the plant when the concentration is set wrongly, that is, set at too high a concentration, at the using time, while it has no effects when the concentration is insufficient. This is commonly said about plant hormones.

In Japanese Patent Publication kokoku No. 16310/1974 referred to above, for example, harms brought by the application of a plant hormone are described as follows: Chlorophenoxyacetic acid-based and β-naphthoxyacetic acid-based compounds are known as so-called plant hormones and application of them to, for example, fruit vegetables, is effective for the growth promotion or fruit time acceleration of the fruit; On the other hand, however, there is a fear of these plant hormones causing various physiological disorders of crops; Such physiological disorders include abnormal bending of the stems or leaves, shrinkage of the leaves, generation of callus on the stems, leaves or peduncles, deformity of fruit, and frequent generation of hollow fruit. It is also described in the above literature that the object of the invention concerned is to provide a fruit-vegetable growth regulator useful in agricultural management, based on the findings that the generation of the above-described physiological disorders can be reduced and at the same time expected effects can be heightened by the mixed use of chlorophenoxyacetic acid-based and/or β-naphthoxyacetic acid-based compound(s) and nucleic acid or decomposition product(s) thereof.

Compared with this, inosine is not a plant hormone, can be used at various application concentrations, does not cause any particular disorders of the plant even used in an excess amount, is made use of by soil microorganisms soon after application and does not cause any obstacles but becomes useful for the soil improvement.

EXAMPLES

The present invention will hereinafter be described in detail by Examples.

Example 1
Preparation of Potted Strawberry Seedlings

In the preparation of strawberry seedlings, it is very important to keep their roots sound during a high-temperature summer season, because the strawberry seedlings are allowed to grow in pots for a long time during this season. Any disorder or putrefaction of the roots has an adverse effect on the subsequent growth after the seedlings are transplanted to the garden, so farmers are most nervous about and also interested in the preparation of potted seedlings out of all their strawberry cultivating works.

Water was sprayed onto potted seedlings of strawberry so as not to allow the water in the pots to run out. Upon spraying, spraying of water having inosine dissolved therein in an amount to give a concentration of 0.05 to 0.5 ppm definitely contributed to the promotion of the growth of the roots (compared with those pots to which inosine-free water was sprayed). Described specifically, when roots are in direct contact with a water-impermeable vinyl or the like at the bottoms of the pots, putrefaction or disorders and blackening thereby of the roots are often observed. The supply of inosine at the above concentration obviously reduced the damage and allowed many new white roots to appear. Thus, a marked difference was recognized compared with the case where inosine had not been administered.

Example 2
Prevention of Bearing-Attributed Exhaustion of Strawberries

About three months after the harvesting of strawberries (i.e., strawberry fruit) was started, symptoms showing bearing-attributed exhaustion were observed. Inosine was therefore applied as a solution thereof in aqueous potassium hydroxide (pH 10.5) to the strawberry plants at their base (i.e., to the strawberry roots), together with a large amount of water to give a concentration of 20 g per 10 ares (about 100 tons of soil). As a result, the strawberries put forth new buds and leaves after several days, while the fruit buds of the strawberries approaching their thickening stage started steady growth. Although the kind of the strawberries tested has a tendency to very strong color development, shortage in coloring matter was not observed.

After that, the harvesting of strawberries was continued favorably. Supported by the sufficient development of leaves, the harvesting of strawberries could be continued until the beginning of June. In addition, until the end of July, runners were obtained from the above parent plants. Even in that season, the strawberries kept their leaves sound with brisk runners.

Example 3
Prevention of Bearing-Attributed Exhaustion of Melons

After the first crop of melons named "PRINCE MELON" (Registered Trade Mark) grown in a green house, an aqueous solution having inosine dissolved therein was administered to the melons at their base (i.e., to the melon roots) to give a concentration of 20 g/10 ares. Only three days after, a number of new white roots were observed to come to appear on the surface when the mulching was uncovered (compared therewith, in a plot where inosine had not been applied, new white roots were hardly even observed when the mulching was turned up). After that, new buds started to show marked growth, floral buds were put forth, and the flowers developed by pollination into fruit buds started thickening.

Such phenomena were also observed from melons grown outdoors. By the administration of inosine to the plot where the melon vines did not creep favorably due to the low temperatures, the melons revived and put forth many floral buds. Besides, thickening of the fruit was satisfactory.

Example 4
Increase of Floral Buds of Lilies

Small-sized lily bulbs are cheap but put forth only one or two flowers per bulb when grown, while large-sized ones are expensive but put forth as many as four or five flowers per bulb.

So, some lily flower cultivators purchase small-sized lily bulbs from lily bulb cultivators, and rear them into large-sized bulbs by cutting off flower buds from lily trees grown from such small-sized bulbs. In the following year, the lily flower cultivators plant such large-sized bulbs, and ship the lily flowers put forth by the large-sized bulbs.

One year, small-sized bulbs of a lily named "RUREIBU" (Trade Mark) were planted. A solution of inosine was administered in an amount of 20 g per 10 ares to the seedling roots, in order to make up for a little delay in permanent planting and also to promote the growth of the seedlings. The seedlings showed a favorable growth and their stems reached a sufficient height. Contrary to expectation, they put forth as many as four floral buds on the average, which were by two more than the ordinary case. The flowers were large and magnificent.

Example 5
Cultivation of *Brassica rapa* var. *pervidis*

In the soil to which inosine had been administered in each amount as shown in Table 1 below, *Brassica rapa* var. *pervidis*, a kind of Chinese cabbage, was planted and 37 days after, it was harvested. The weight of the roots was weighed after heat-drying. To the control plot, no inosine was added. Incidentally, the soil was prepared by sifting a soil called Kanumatsuchi through a 4-mesh sieve and then adding "Esusan Fertilizer", an amino-acid based, commercial fertilizer, ex Ajinomoto Co., Inc., to the sifted soil of all the test plots, in an amount of 1200 mg per 400 g-soil. Measurement results of the weight of the roots are shown together in the table.

TABLE 1

| Administered Amount (ppm) | Weight of the roots (g) | Ratio (%) |
| --- | --- | --- |
| 0 (Control plot) | 0.19 | 100 |
| 0.05 | 0.28 | 147 |
| 0.1 | 0.27 | 142 |
| 0.2 | 0.33 | 174 |
| 0.3 | 0.29 | 153 |
| 0.5 | 0.45 | 237 |

As shown in Table 1, the roots of *Brassica rapa* var. *pervidis* showed a marked growth by the administration of inosine in an amount of at least 0.05 ppm, preferably 0.5 ppm, relative to the soil.

A photograph of the water-washed roots of *Brassica rapa* var. *pervidis* harvested as described above was taken. Although this photograph does not clearly show the difference in the growth of the above-ground parts of *Brassica rapa* var. *pervidis* between the inosine-added plots and the control plot, the growth in the test plots was superior to that of the control plot in the subterranean parts, more specifically, superior in the length and the number of the roots and moreover, in the quality of the above-ground parts (leaf part) as leaf vegetable. Thus, it has been found that the addition of inosine was effective even in an amount of only 5 to 20 g per 100 t of soil.

Example 6
Prevention of Damping-Off and Improvements in Sweetness Degree of Melons In the case where late-autumn netted melon is subjected to fix planting in early September in a warm district such as Kyushu, Japan, it cannot endure the thickening of the fruit in November or so at the harvest time and often experiences damping-off in a moment. The damping-off causes awful damage and, for example, it usually damages all the melons in a green house within as few as 2 to 3 days. The damping-off is presumed to occur because if cultivation is continued without sufficient extension of the roots at the warm time, demand for nutrients or water more than expected occurs at the thickening time of the fruit but the roots cannot meet the demand.

In each of an inosine-applied plot and an inosine-free control plot of the same field, 10 seedlings of an EARLS series netted melon were planted. In the inosine-applied plot, 20 g per 10 ares (corresponding to about 100 t of soil) of inosine were applied to the melon roots several times, as an aqueous solution adjusted to pH 10.5 with potassium hydroxide, together with a large amount of water at an early stage of cultivation, and the melons were allowed to grow. As a result, 20 to 30% of the melon trees experienced damping-off. They did not, however, show complete death but partial death in their leaves. The melons kept alive with withered leaves and 10 melons were harvested from the 10 trees.

On the other hand, in the control plot to which inosine had not been applied, many melon trees experienced damping-off. Six trees damped off completely, and harvested therefrom were four melons, which were less than half of the melons in the inosine-applied plot. Concerning the growth of the roots, the inosine-applied plot ((a)) was superior to the control plot ((b): inosine-free plot (control plot)) in the thickness of the roots.

The inosine-applied plot was also higher in the sweetness degree (i.e., sugar contents or Brix degree) of the fruit. Described specifically, three delicious-looking, fine-shaped melons were selected from the melons harvested from each of the inosine-applied plot and the inosine-free plot, and their sweetness degree was evaluated by 10 people. As a result, all the members evaluated that the melons from the inosine-applied plot had stronger sweetness and were delicious compared with those from the control plot.

Example 7
Cultivation Test (in pots) of a *Chrysanthemum coronarium*

The cultivation test of a *Chrysanthemum coronarium* (a new root-spread, medium-sized leaved *Chrysanthemum coronarium*) was conducted by Japan Fertilizers and Foods Association.

(a) Testing Method

Seedling raising pots (size: 9×7.5 cm, made of polyethylene) were filled with soil to be tested, followed by the addition of a common fertilizer and water to artificially prepare a garden condition. When rooting was recognized after the seed sowing of the *Chrysanthemum coronarium*, a predetermined amount of an inosine solution was applied and the application effects on roots, above-ground parts such as stems and leaves were studied.

(b) Testing (1) A 2% solution of inosine was applied after dilution with pure water. The application amount of each test plot is shown in Table 2 below.

TABLE 2

| Test plot | Administered amount (per 100 t - soil) |
|---|---|
| Standard amount | 5 (g) |
| 2-fold amount | 10 |
| 4-fold amount | 20 |
| 6-fold amount | 30 |
| 10-fold amount | 50 |

(2) The progress including field husbandry is shown in Table 3 below.

TABLE 3

| Events | Date |
|---|---|
| Pots filled with soil | December 1, 1996 |
| Fertilized and watered | December 1, 1996 |
| Sowing (10 seeds per pot) | December 1, 1996 |
| Thinning out the seedlings to three | December 10 1996 |
| Inosine administered | December 15, 1996 |
| End of test, Observation | January 13, 1997 |

Incidentally, to all the test plots, aqueous solutions of monoammonium phosphate, ammonium sulfate and potassium chloride were added in amounts each corresponding to 20 mg in terms of N, $P_2O_5$ and $K_2O$. Cultivation was carried out in a heated green house. At the application time of inosine, the seedlings had two leaves and reached a plant length of 5 cm. The cultivation was conducted for 44 days in total, including 25 days after the application of inosine.

(c) Test Results

Test results are shown in Table 4 below.

TABLE 4

| Test pots | | No. | Above-ground parts (stems and leaves) Weight (g) (Ratio) | Subterranean parts (roots) Weight (g) (Ratio) |
|---|---|---|---|---|
| Inosine Administration | Standard amount | 1 | 3.5 | 0.7 |
| | | 2 | 3.4 | 1.0 |
| | | 3 | 3.4 | 0.8 |
| | | Average | 3.43 (103) | 0.83 (108) |

TABLE 4-continued

| Test pots | | No. | Above-ground parts (stems and leaves) Weight (g) (Ratio) | Subterranean parts (roots) Weight (g) (Ratio) |
|---|---|---|---|---|
| | 2-fold amount | 1 | 4.1 | 1.1 |
| | | 2 | 4.1 | 0.9 |
| | | 3 | 3.7 | 1.2 |
| | | Average | 3.97 (119) | 1.07 (139) |
| | 4-fold amount | 1 | 4.6 | 1.0 |
| | | 2 | 4.3 | 1.4 |
| | | 3 | 4.4 | 1.3 |
| | | Average | 4.43 (133) | 1.23 (160) |
| | 6-fold amount | 1 | 3.9 | 1.1 |
| | | 2 | 4.2 | 1.1 |
| | | 3 | 4.4 | 1.1 |
| | | Average | 4.17 (125) | 1.10 (143) |
| | 10-fold amount | 1 | 3.6 | 1.2 |
| | | 2 | 3.8 | 0.9 |
| | | 3 | 3.9 | 1.0 |
| | | Average | 3.77 (113) | 1.03 (134) |
| Non-administered pot (Control pot) | | 1 | 3.5 | 0.8 |
| | | 2 | 3.0 | 0.7 |
| | | 3 | 3.5 | 0.8 |
| | | Average | 3.33 (100) | 0.77 (100) |

It is apparent that application effects of inosine are recognized in the growth of the roots and foliar (above-ground) parts of *Chrysanthemum coronarium*.

Example 8

Cucumbers

In this example were employed pots and a bed soil exclusively used for raising seedlings, which were to show the application effects of inosine clearly.

(a) Test Method

"Sakata's Cell Pots (exclusively used for raising seedlings)" and a bed soil exclusively used for cell pots, the filled amount being 17 g per pot, were employed as the pots and the bed soil. Neither the test plots nor the control plot were subjected to fertilization. Inosine was applied three days after the beginning of germination. The seeds were sown on Sep. 19, 1996, inosine was applied on September 23, and the investigation on the harvest was carried out on October 1st.

(b) Designing of Test Plots

Test plots were designed as shown in Table 5 below.

TABLE 5

| Test plots | Administration of inosine |
|---|---|
| Control plot | — |
| 5 g inosine-per-10-are plot | 8.5 ml of a 0.01 mg/dl solution |
| 20 g inosine-per-10-are plot | 3.4 ml of a 0.1 mg/dl solution |
| 30 g inosine-per-10-are plot | 5.1 ml of a 0.1 mg/dl solution |
| 50 g inosine-per-10-are plot | 8.5 ml of a 0.1 mg/dl solution |

(c) Results

Results are shown in Table 6 below. Concerning each plot, the above-ground parts (height and weight) and subterranean parts (root weight) of 8 cucumber seedlings were measured and the average values were calculated, which are shown in Table 6 below. Incidentally, the roots were weighed after dried.

TABLE 6

| | Check items | | |
|---|---|---|---|
| | above-ground parts | | subterranean parts |
| Test plots | height (ratio) | weight (ratio) | root weight (ratio) |
| Control plot | 8.44(100) | 0.91(100) | 0.023(100) |
| 5 g inosine-per-10-are plot | 10.96(130) | 0.97(107) | 0.031(135) |
| 20 g inosine-per-10-are plot | 12.10(143) | 1.06(116) | 0.033(143) |
| 30 g inosine-per-10-are plot | 11.72(139) | 1.13(124) | 0.026(113) |
| 50 g inosine-per-10-are plot | 10.68(127) | 1.02(112) | 0.027(117) | height unit: cm
weight unit: g per sample
root weight unit: g per sample

It can be seen from the above table that the inosine-applied plots were superior to the control plot (inosine-application-free plot) in every item. Application of inosine in an amount of 20 to 30 g/10 ares is presumed to be the most effective.

Example 9 Peas

Peas were subjected to the cultivation test in the same manner as in Example 8. Supposing that the weight of the combined vine and foliar weight and that of the roots of the control peas (application-free plot) were 100 each, the vine and foliar weights were 107 and 120 and the root weights were 120 and 120 when inosine was applied in amounts of 30 g/10 ares and 50 g/10 ares, respectively. Thus, application effects of inosine were recognized.

EFFECTS OF THE INVENTION

The present invention has made it possible to carry out plant-root growth promotion easily and, in turn, to carry out rearing or thickening of leaves, floral buds, fruit bearing, or fruit easily.

What is claimed as new and desired to be secured by Letters Patent of the United Patents is:

1. A method for promoting root growth of a plant, which comprises applying inosine to soil in an amount of 5–50 g per 100 tons of soil (0.05–0.5 ppm), or to hydroponic water in a concentration of 0.1–2 ppm based on the hydroponic water, the plant being in said soil, or in said hydroponic water, and being selected from the group consisting of leaf vegetables, fruit vegetables, root vegetables, flowers, fruit trees and grains.

2. The method of claim 1, wherein said inosine is applied to soil containing said plant.

3. The method of claim 1, wherein said inosine is applied to hydroponic water containing said plant.

4. The method of claim 1, wherein said inosine is applied in an alkaline aqueous solution.

5. The method of claim 4, wherein said alkaline aqueous solution contains inorganic alkali.

6. The method of claim 4, wherein said alkaline aqueous solution contains a basic amino acid.

7. The method of claim 5, wherein said inorganic alkali is potassium hydroxide.

8. The method of claim 1, wherein said plant is a strawberry or melon plant, and said method further treats fruit-bearing exhaustion of said plant.

9. The method of claim 1, wherein said plant is a lily, and said method further increases floral buds of said lily.

10. The method of claim 1, wherein said plant is a chinese cabbage.

11. The method of claim 8, wherein said plant is a melon plant, and said method further increases sugar content of melons of said plant.

12. The method of claim 1, wherein said plant is a chrysanthemum.

13. The method of claim 6, wherein said basic amino acid is lysine or arginine.

* * * * *